(12) United States Patent
Yamamoto

(10) Patent No.: US 6,514,269 B2
(45) Date of Patent: Feb. 4, 2003

(54) ENDOSCOPIC TREATING INSTRUMENT

(75) Inventor: Tetsuya Yamamoto, Hidaka (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/873,624

(22) Filed: Jun. 4, 2001

(65) Prior Publication Data

US 2002/0013595 A1 Jan. 31, 2002

(30) Foreign Application Priority Data

Jun. 13, 2000 (JP) .......................................... 2000-177315
Feb. 16, 2001 (JP) .......................................... 2001-039668

(51) Int. Cl.[7] .............................................. A61B 17/20
(52) U.S. Cl. ........................................ 606/170; 606/205
(58) Field of Search ................................ 606/167, 170, 606/172, 174, 205, 206, 207, 208, 209, 210, 159; 604/22

(56) References Cited

U.S. PATENT DOCUMENTS

| 4,662,371 | A | | 5/1987 | Whipple et al. | |
|---|---|---|---|---|---|
| 5,152,780 | A | * | 10/1992 | Honkanen et al. | 600/564 |
| 5,556,407 | A | * | 9/1996 | Wurster et al. | 30/134 |
| 5,620,415 | A | * | 4/1997 | Lucey et al. | 604/22 |
| 5,782,834 | A | * | 7/1998 | Lucey et al. | 604/22 |
| 5,899,914 | A | * | 5/1999 | Zirps et al. | 606/170 |
| 6,062,973 | A | * | 5/2000 | Baertlein | 30/228 |
| 6,077,287 | A | * | 6/2000 | Taylor et al. | 606/170 |

FOREIGN PATENT DOCUMENTS

| FR | 2 778 839 | 11/1999 |
|---|---|---|
| JP | 11-76244 | 3/1999 |

* cited by examiner

*Primary Examiner*—Danny Worrell
(74) *Attorney, Agent, or Firm*—Scully, Scott, Murphy & Presser

(57) ABSTRACT

An endoscopic treating instrument such as a bioptome has cup portions including inner cutting blades on the rims. The angle of inner cutting blade is 85° or more. Due to such cutting blade, tissue uneasily slides thereon and the cup portions can bite tissue more effectively. Therefore, the amount of obtained tissue can be increased.

20 Claims, 16 Drawing Sheets

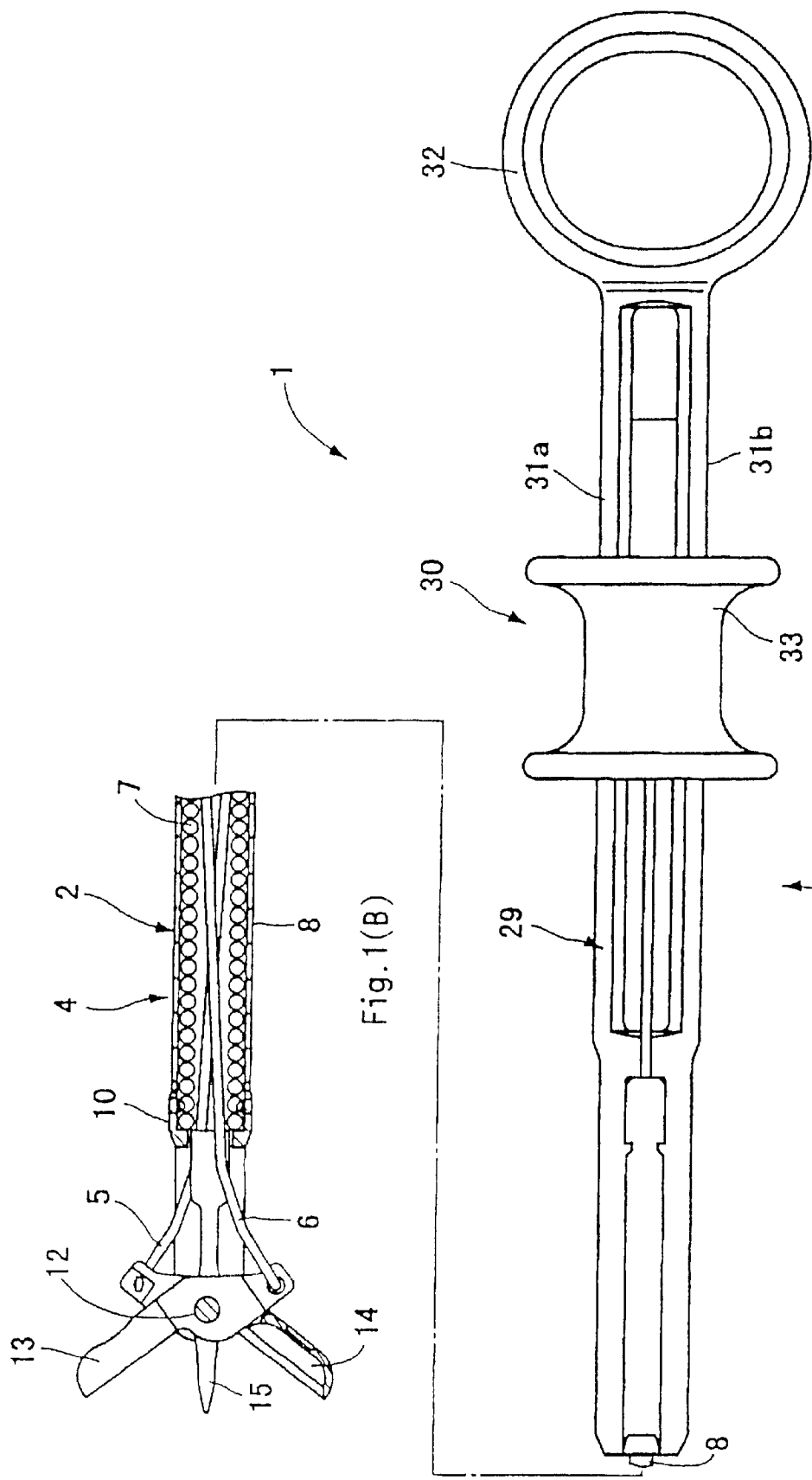

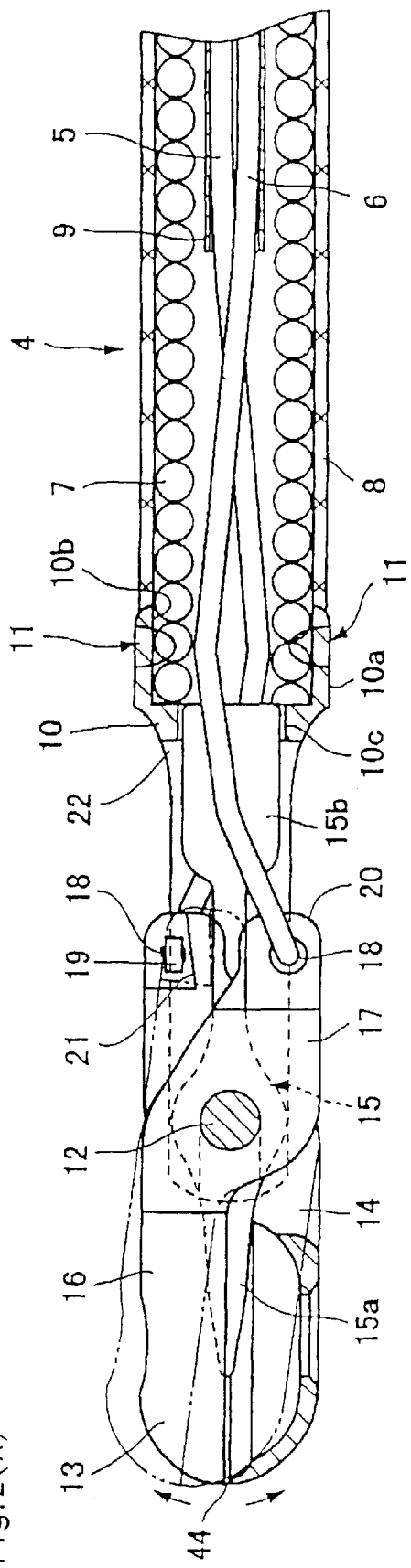
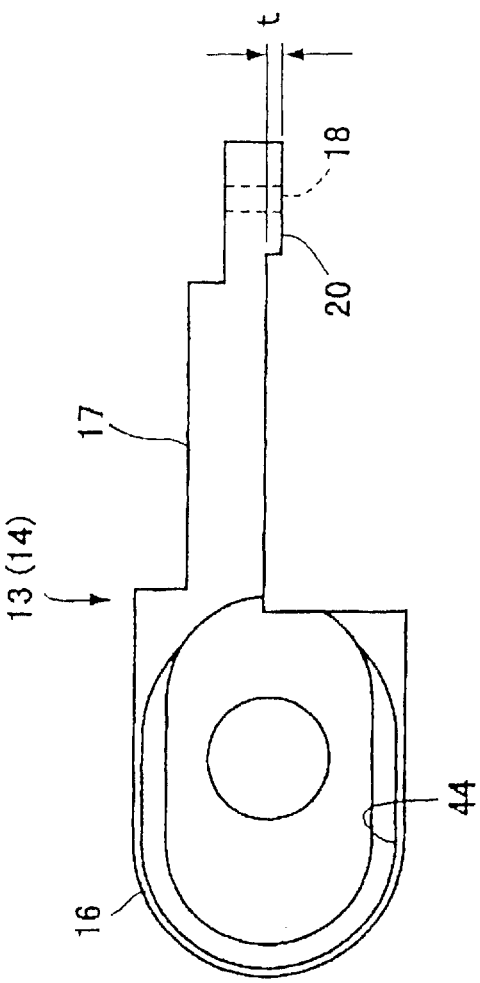
Fig.2(A)
Fig.2(B)
Fig.2(C)

Fig.3
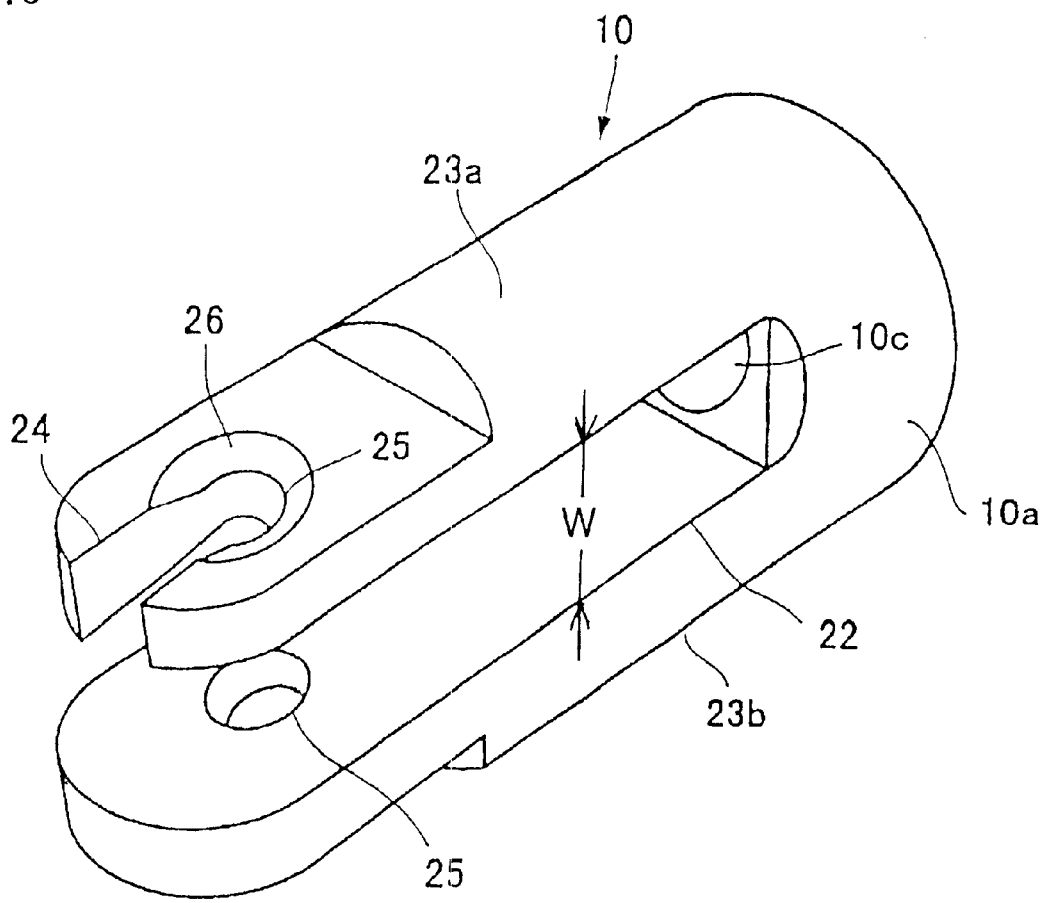
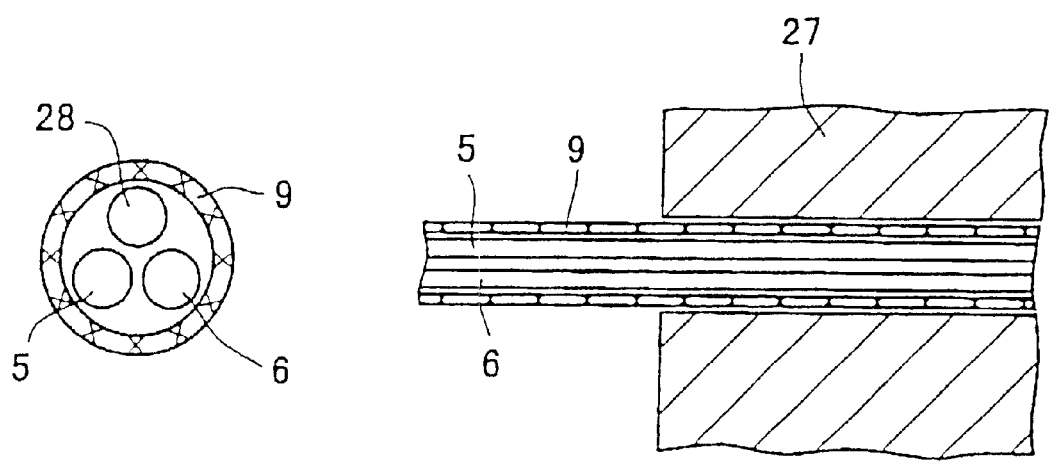
Fig.4(A)   Fig.4(B)

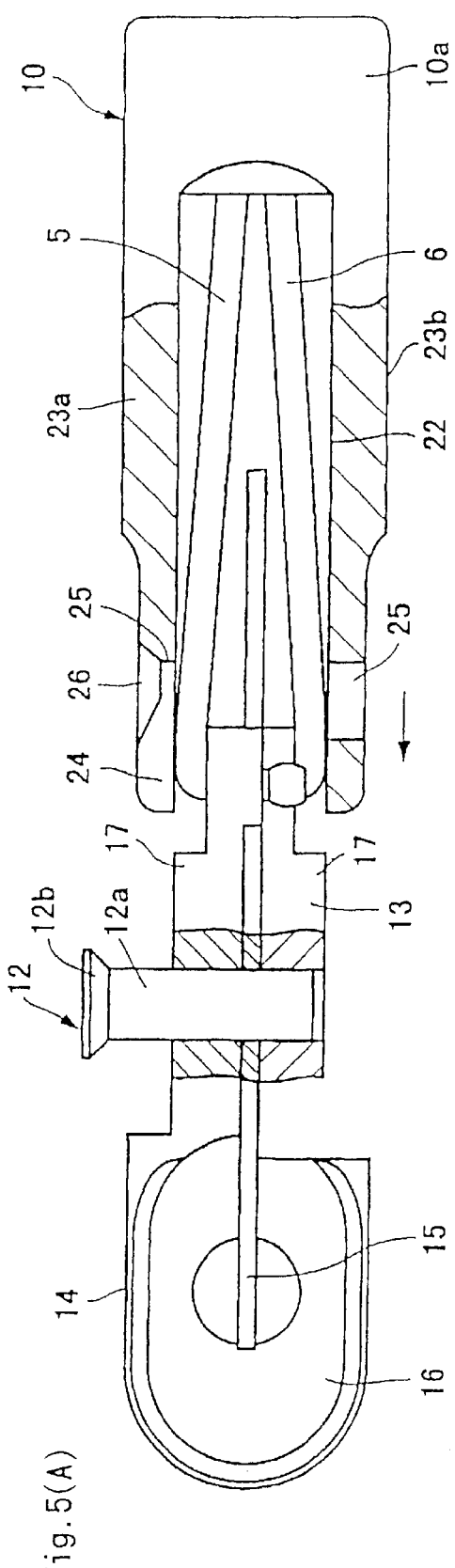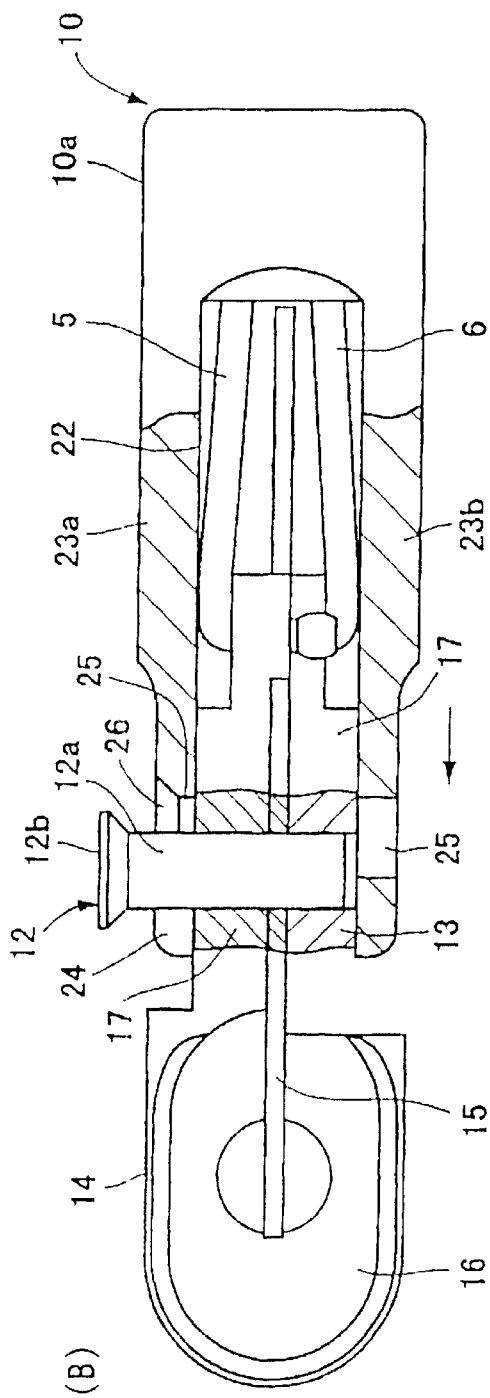
Fig.5(A)
Fig.5(B)

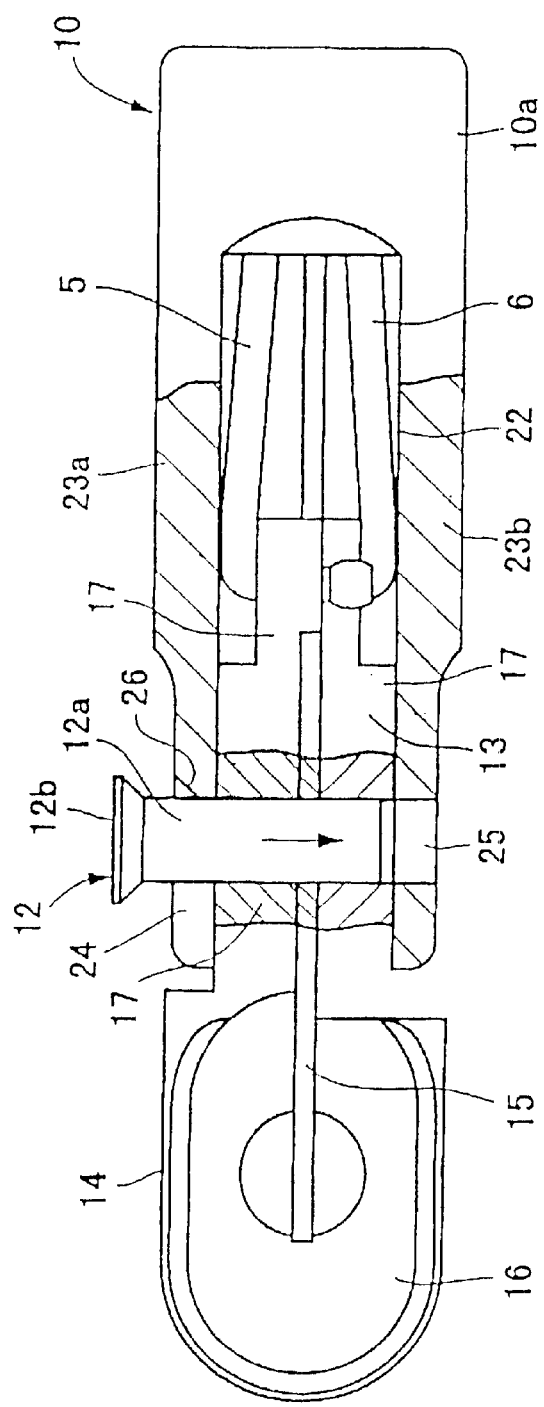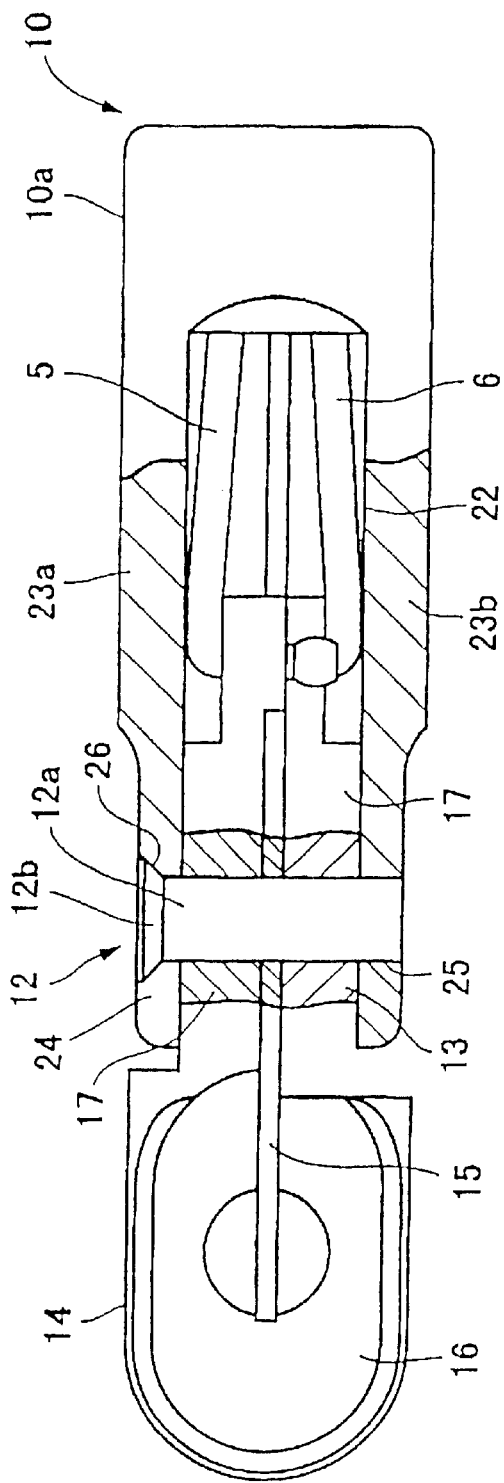
Fig.6(A)
Fig.6(B)

ENDOSCOPIC TREATING INSTRUMENT

CROSS-REFERENCE TO RELATED APPLICATIONS

This application is based upon and claims the benefit of priority from Japanese Patent Applications No. 2000-177315 filed on Jun.13, 2000 and No. 2001-39668 filed on Feb. 16, 2001 in Japan, the entire contents of which are incorporated by reference.

BACKGROUND OF THE INVENTION (1) Field of the Invention

This invention relates to an endoscopic treating instrument inserted into the body through an endoscope channel in order to obtain tissue inside the body cavity.

(2) Description of the Related Art

Generally, as shown in FIG. 24, a biopsy endoscopic treating instrument has bioptome members including cup portions 101. The cup portions are able to open and close and are provided on the distal end of a flexible elongated insertion part inserted into the body through an endoscope channel. In addition, such instrument has a member operating the opening and the closing of the cup portions 101 at the proximal end of the insertion part.

An insertion part has an outer tube and an operation wire arranged movably in the axial direction of the insertion part in the hollow of the outer tube. The bioptome member is connected to the distal end of the operation wire. An operation member of an operation part moves the operation wire forward and backward. The wire movement remotely causes to open and close the cup portion 101 of the bioptome member.

In FIG. 25, for example, Japanese Patent Laid-Open Publication No.11-76244 shows an endoscopic treating instrument having inner cutting blades 103 along the rim of an opening 102 inside cup portion 101. These cutting blades 103 are tapered about 45–70° relative to a plane 104 along the rim of the opening 102.

As shown in FIG. 24, tissue 105 is captured and a part thereof is accommodated between the two cup portions 101 to use a bioptome. In this state, the closure of the two cup portions 101 causes the inner cutting blades 103 of the cup portions 101 to cut the tissue 105.

In the above-mentioned Japanese Patent Laid-Open Publication No.11-76244, the cutting blades 103 of the cup portions 101 have an angle of about 45–70°. As shown in FIG. 25, such angle results in a comparatively small angle θ 1 with which the cutting blades 103 bite tissue 105. Therefore, the inner cutting blades 103 easily slip on tissue 105 and the tissue 105 falls off the cup portions 101 of a bioptome. Accordingly, the amount of taken tissue 105 tends to be small.

In view of the foregoing, an object of the present invention is to provide an endoscopic treating instrument wherein inner cutting blades along the rim of cup portion uneasily slip on and tightly bite tissue to increase the amount of taken tissue.

SUMMARY OF THE INVENTION

Accordingly, an endoscopic treating instrument is provided. The endoscopic treating instrument comprises: a flexible insertion part having a hollow section; an operation wire provided in the hollow section of said insertion part and movable forward and backward in the axial direction of said insertion part; an operation part which is connected to the proximal end of said insertion part for moving said operation wire forward and backward; and a bioptome member mounted to the distal end of said insertion part, said bioptome member having a cup portion, said cup portion having an inner cutting blade formed on a rim thereof, an angle θ of said cutting blade being formed from about 85° to about 110° to a plane along the rim of said cup portion.

Also provided is an endoscopic treating instrument comprising: a body; at least one member pivotally connected to a distal end of said body, each of said at least one member further having a cup portion defined by a rim, said rim having an inner cutting blade formed at least partly thereon, an angle θ of said cutting blade being formed from about 85° to about 110° to a plane along said rim of said cup portion.; and a handle part having means for actuating said at least one member between open and closed positions.

BRIEF DESCRIPTION OF THE DRAWINGS

These and other features, aspects, and advantages of the apparatus and methods of the present invention will become better understood with regard to the following description, appended claims, and accompanying drawings where:

FIG. 1(A) illustrates a side view of an endoscopic bioptome according to the first embodiment of the present invention.

FIG. 1(B) illustrates the distal end of the endoscopic bioptome of FIG. 1(A) shown in an open position.

FIG. 2(A) illustrates an enlarged vertical section showing the end portion of an insertion part of the endoscopic bioptome.

FIG. 2(B) illustrates a front view of bioptome cups of FIG. 2(A).

FIG. 2(C) illustrates a plan view of the bioptome cup according to the endoscopic bioptome of FIG. 2(A).

FIG. 3 illustrates a perspective view showing a cup holding member of the bioptome according to the first embodiment.

FIG. 4(A) illustrates a transverse sectional view showing two operation wires and one dummy wire in the hollow of an inner tube of the insertion part.

FIG. 4 (B) illustrates a vertical section wherein an extrusion tube molding is integrally assembling the inner tube and the operation wires.

FIGS. 5(A) and 5(B) illustrate the assembling procedure with which the bioptome cups and the cup holding member of bioptome are assembled, where FIG. 5(A) illustrates a vertical section showing the state wherein bioptome cups and a needle are temporarily assembled with a pin, and FIG. 5(B) illustrates a vertical section wherein the solid shaft of the pin is slid into a slit in the cup holding member.

FIG. 6(A) illustrates a vertical section wherein after a solid shaft of the pin of the bioptome cups of a bioptome according to the first embodiment slides into the slit of the cup holding member, the shaft and a bore are fit.

FIG. 6(B) illustrates a vertical section wherein a countersink part of the pin and a dish receiving portion of the cup holding member, which are engaged, are joined to the cup holding member.

DETAILED DESCRIPTION

Figure 7A:
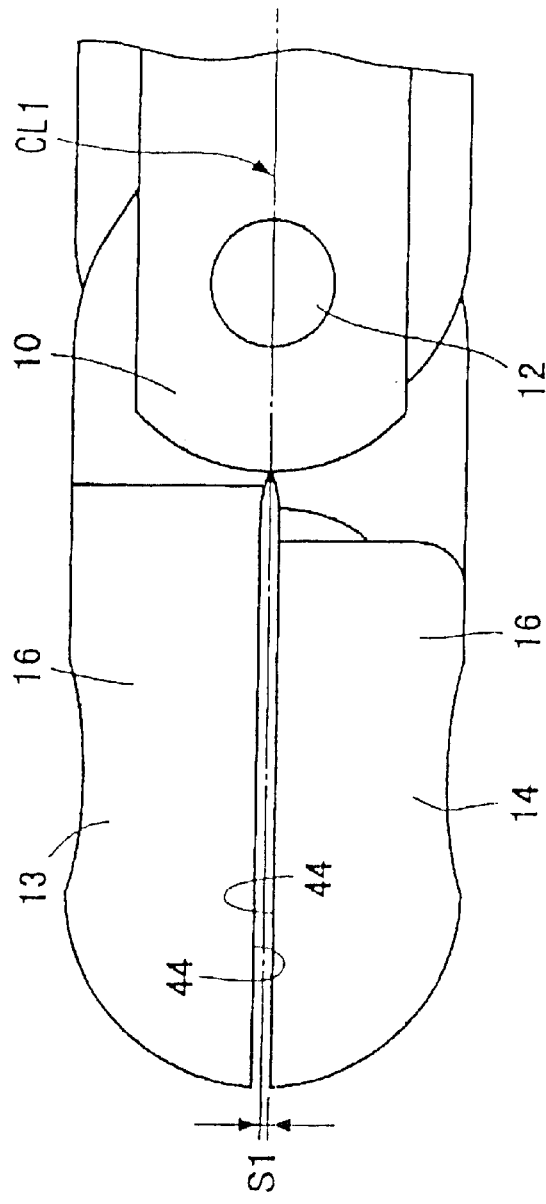
FIG. 7(A) illustrates a side view wherein the face of a cutting blade is slightly offset from the center line of the pin in the bioptome cups of the bioptome according to the first embodiment.

The first embodiment of the present invention is now explained with reference to FIGS. 1–12. FIGS. 1(A) and 1(B) show an endoscopic bioptome 1 as an endoscopic treating instrument according to the first embodiment. In the embodiment, the bioptome 1 is given by way of example only and not to limit the scope of the present invention. Those skilled in the art will appreciate that other endoscopic treating instruments, such as hot biopsy forceps and holding forceps may also be used without departing from the scope or spirit of the present invention.

The endoscopic bioptome 1 according to the first embodiment has a flexible elongated insertion part 2 (generally referred to as a body) inserted into a human body through an endoscope channel (not shown), and a proximal operation part 3 connected to the proximal end of the insertion part 2.

Furthermore, the insertion part 2 includes an exterior tube 4 and two operation wires 5, 6 that are located in the hollow of the exterior tube 4 and movable forward and backward in the axial direction of the insertion part 2. As shown in FIG. 2(A), the exterior tube 4 has a tightly wound coil 7, an outer tube 8 covering the outer surface of the coil 7 which is preferably tubing or heat shrinkable tubing and an inner tube 9 arranged inside the coil 7.

The proximal end of a cup holding member 10 is engaged with the distal end of the coil 7. A cup holding member 10 has a slit 22 as will be described below. There is a possibility that the cup holding member 10 can damage the inner surface of an endoscope channel when the member 10 is inserted into the endoscope channel. Preferably, the edge of the cup holding member 10 is as spherical as possible for avoiding such damage. If the edge of the cup holding member 10 is removed by centrifugal barrel grinding with a grind stone after the cutting, damage to the inner surface of the endoscope channel is less likely. If the proximal end of the slit 22 is rounded, the inner surface of the endoscope channel is prevented from damage. The cup holding member 10 has an engaging portion 10a engaging the distal end of the coil 7 on the proximal end thereof. A coil hole 10b into which the distal end of the coil 7 is inserted is formed on the proximal side of the engaging portion 10a. A needle hole 10c which is smaller than the coil hole 10b is formed on the distal side of the engaging portion 10a. The cup holding member 10 is engaged with the coil 7 with the distal end of the coil 7 being inserted into the coil hole 10b formed in the engaging portion 10a of the cup holding member 10. Moreover, the engaging portion 10a of the holding member 10 is then preferably secured to the distal end of the coil 7, preferably by welding, such as by laser welding. Through a welded portion 11 by laser welding, the cup holding member 10 is fixed to the distal end of the coil 7.

On the distal end, the insertion part 2 has a pair of bioptome cups (bioptome members) 13, 14 which are rotatably connected around a pin 12 fixed to the distal end of the cup holding member 10 and a needle member 15 arranged to be between the bioptome cups 13 and 14.

A sharp needle portion 15a of the needle member 15 protrudes, on the distal side of the portion fixed by the pin 12. On the proximal side of the needle member 15, an engaging portion 15b is inserted into the needle hole 10c of the engaging portion 10a in the cup holding member 10. If unnecessary, the needle member 15 may not be provided.

The two bioptome cups 13 and 14 are preferably similar in structure. Therefore, only the structure of cup 13 is described herein. For the other cup 14, same reference numerals denote the corresponding elements and a detail description is omitted.

As shown in FIG. 2(C), the bioptome cup 13 has a cup portion 16 and an arm portion 17 connected to the proximal side of the cup portion 16. A hole 18 for fixing a wire is formed on the proximal end of the arm portion 17. The distal end of the operation wire 6 is inserted into and fixed to the hole 18 of the bioptome cup 13, meanwhile the distal end of the operation wire 5 is inserted into and fixed to the hole 18 of the other bioptome cup 14. In addition, the operation wires 5 and 6 have a stopper 19 so that the distal ends of operation wires 5 and 6 will not detach from the holes 18.

A reinforcing thick portion 20 wherein the thickness T of the proximal end of the arm portion 17 is added is formed around the holes 18 of the bioptome cups 13 and 14 so that the arm portions 17 will not be broken even if an excessive force is applied to the operation wires 5 and 6. Furthermore, a taper 21 is provided at a portion interfering with the needle member 15, in the proximal end of the arm portion 17 so that the bioptome cups 13, 14 can rotate somewhat even when the cups 13, 14 are closed.

As shown in FIG. 3, a slit 22 is formed in the distal end of the cup holding member 10. As shown in FIGS. 5(A), 5(B), 6(A) and 6(B), the slit 22 has a width (W) so that the needle member 15 can be inserted into the slit 22 as fastened by the arm portions 17 of the bioptome cups 13, 14. And the proximal end of the slit 22 extends close to the engaging portion 10a on the proximal side. On both sides of the slit 22, connecting arms 23a, 23b are preferably parallel.

A second slit 24 is formed on the distal end of the connecting arm 23a. The slit 24 is so designed such that a solid shaft 12a of the pin 12 can penetrate. The pin 12 includes a countersink part 12b having a larger diameter than that of the solid shaft 12a, on one end of the solid shaft 12a.

Insertion holes 25 for the pin 12 are formed at corresponding positions in the two connecting arms 23a, 23b of the cup holding member 10. The insertion hole 25 of the connecting arm 23a is linked to the proximal end of the slit 24. The connecting arm 23a has a countersink-receiving portion 26 that engages the countersink part 12b of the pin 12 around the rim of the insertion hole 25.

In the assembly of the members around the distal end of the insertion part 2, as shown in FIG. 5(A), the bioptome cups 13, 14 and the needle member 15 are temporarily assembled to form a temporarily assembled unit. Then, the temporary unit is set to the cup holding member 10. While the solid shaft 12a of the pin 12 slides along the slit 24 of the cup holding member 10 as shown in FIG. 5(B), the solid shaft 12a is located in the insertion hole 25 as shown in FIG. 6(A). Subsequently, as shown in FIG. 6(B), the countersink part 12b of the pin 12 is engaged with the countersink-receiving portion 26 of the cup holding member 10. The solid shaft end face opposite to the countersink part 12b in the pin 12 is joined to the cup holding member 10 by any means known in the art such as by laser welding, caulking, blazing, soft soldering, ultrasonic welding in which metals are welded by ultrasonic vibration.

The proximal ends of the operation wires 5, 6 in the hollow of the exterior tube 4 extend toward the operation part 3 on the proximal side. In order to assemble the inner tube 9 and the operation wires 5, 6 in the exterior tube 4, the operation wires 5, 6 may be inserted into the hollow of the inner tube 9. As shown in FIG. 4(B), it is possible that an extrusion tube molding 27 is used to form the inner tube 9 with the operation wires 5, 6 being a core and to integrate the operation wires 5, 6 and the inner tube 9. In this case, the operation wires 5, 6 do not adhere to the inner tube 9, in order that the operation wires 5, 6 can slide in the hollow of the inner tube 9.

Moreover, as shown in FIG. 4 (A), one dummy wire 28 may be added to the operation wires 5, 6 in the inner tube 9 so that the inner tube 9 can be as circular as possible when the inner tube 9 is formed by the extrusion tube molding 27. The number of dummy wires 28 can be one or more as needed. The dummy wire 28 is removed from the inner tube 9 which the wires are embedded in and which are cut in the finished dimension, after the molding.

As shown in FIGS. 1(A) and 1(B), the operation part 3 includes a main body 29 and a slider (operation member) 30. The main body 29 has two guide rail portions 31a, 31b axially extending in order to slidingly guide the movement of slider 30. In addition, the proximal end of main body 29 has a ring 32 in which fingers are inserted.

Figure 8:
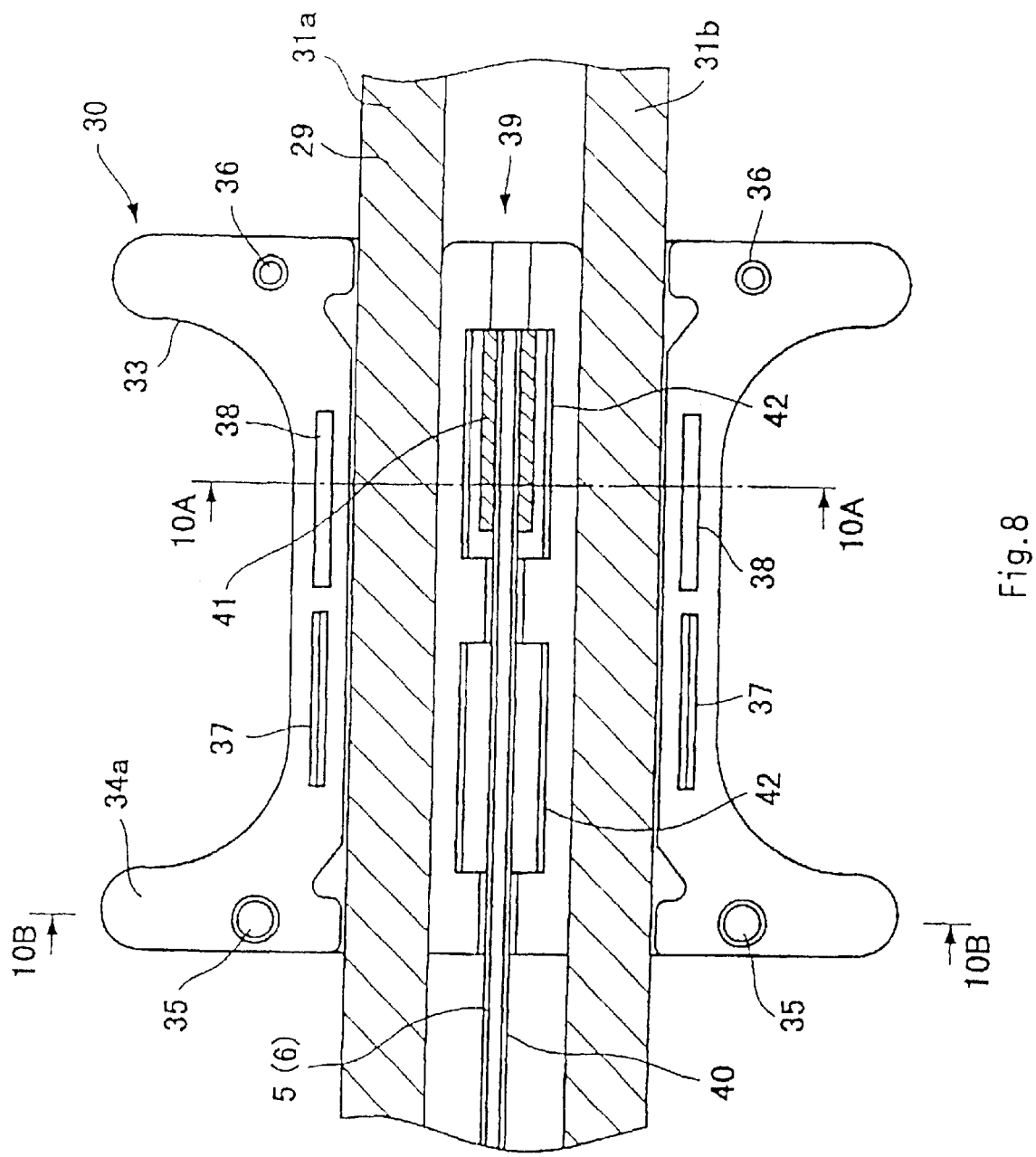
FIG. 8 illustrates a vertical section wherein a slider is set to the main body of operation part in the bioptome according to the first embodiment.
Figure 9:
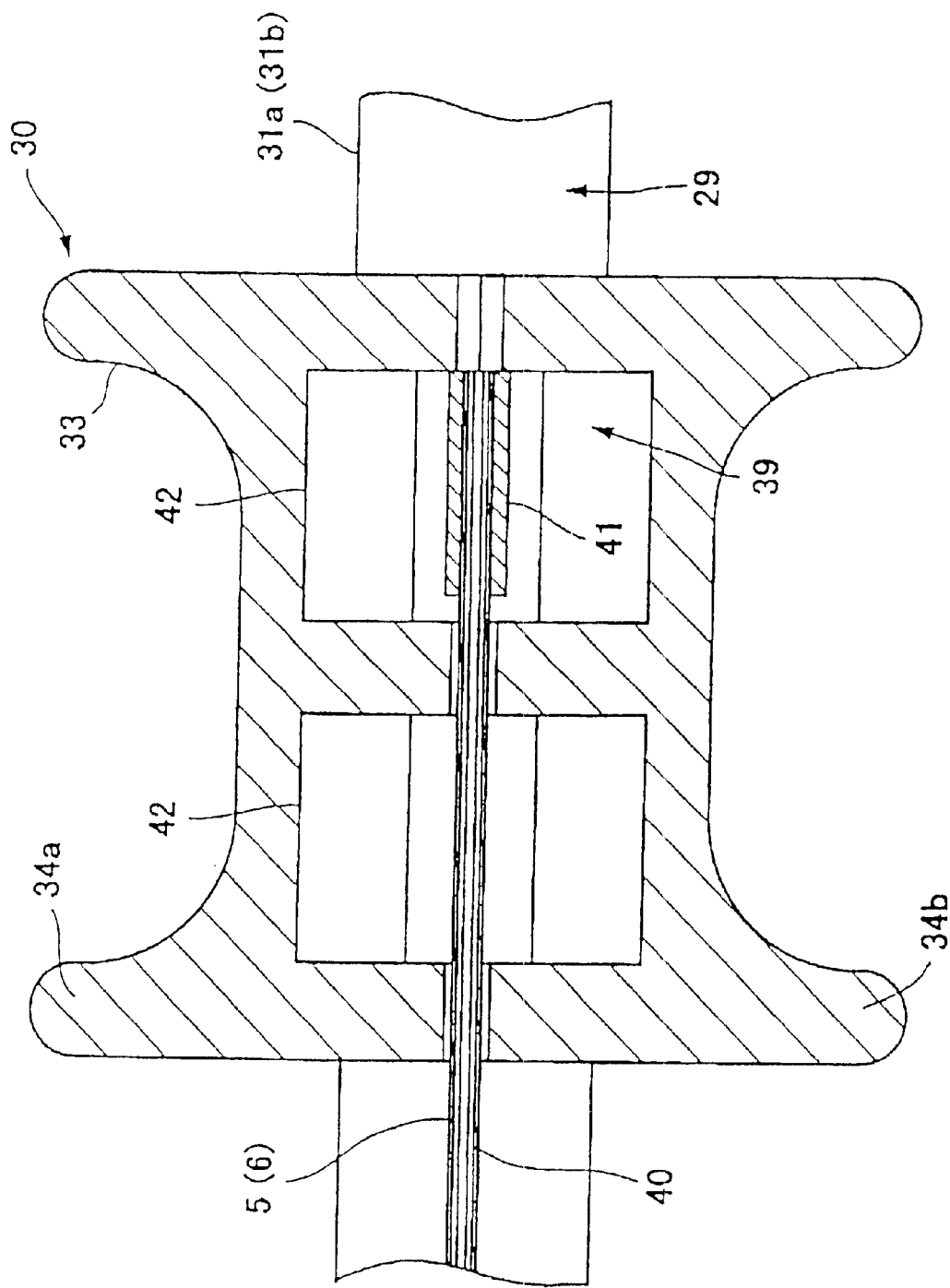
FIG. 9 illustrates a vertical section wherein the section in FIG. 8 is rotated at 90°.

The slider 30 has a slider main body 33 which is substantially cylindrical and which axially moves along the guide rail portions 31a, 31b of the main body 29. As shown in FIGS. 10 (A) and 10(B), the slider main body 33 has two slider members 34a, 34b, each of which are preferably half-circular in shape and are joined. As shown in FIG. 8, a cavity 35 and an engaging projection 36 are symmetrically provided two by two on the joint faces of the two members 34a, 34b. Moreover, a projection 37 and a cavity 38 for ultrasonic welding are symmetrically provided two by two.

Figure 10A:
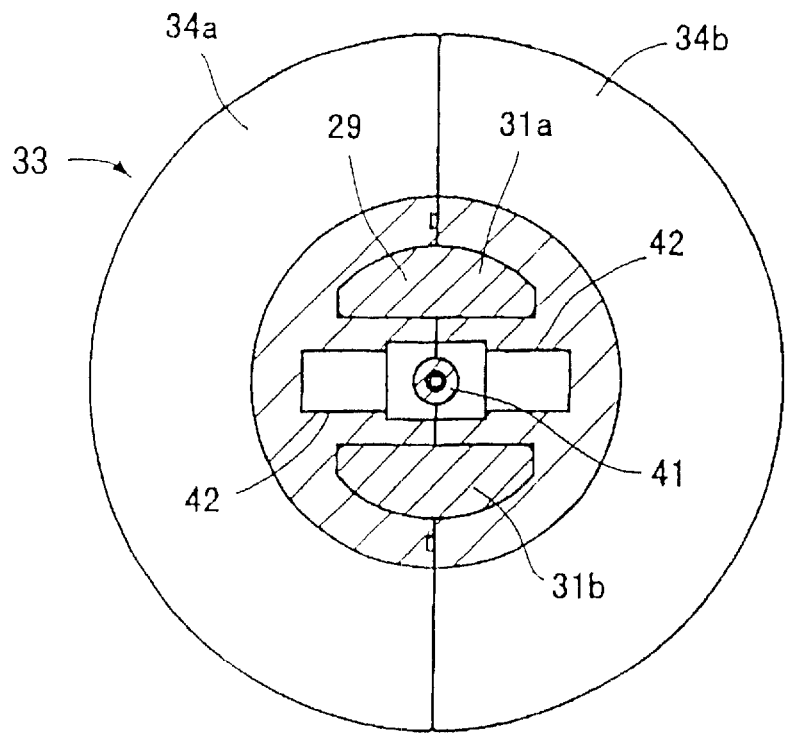
FIG. 10(A) illustrates a sectional view of the slider and the operation part of FIG. 8 taken along line 10A—10A.
Figure 10B:
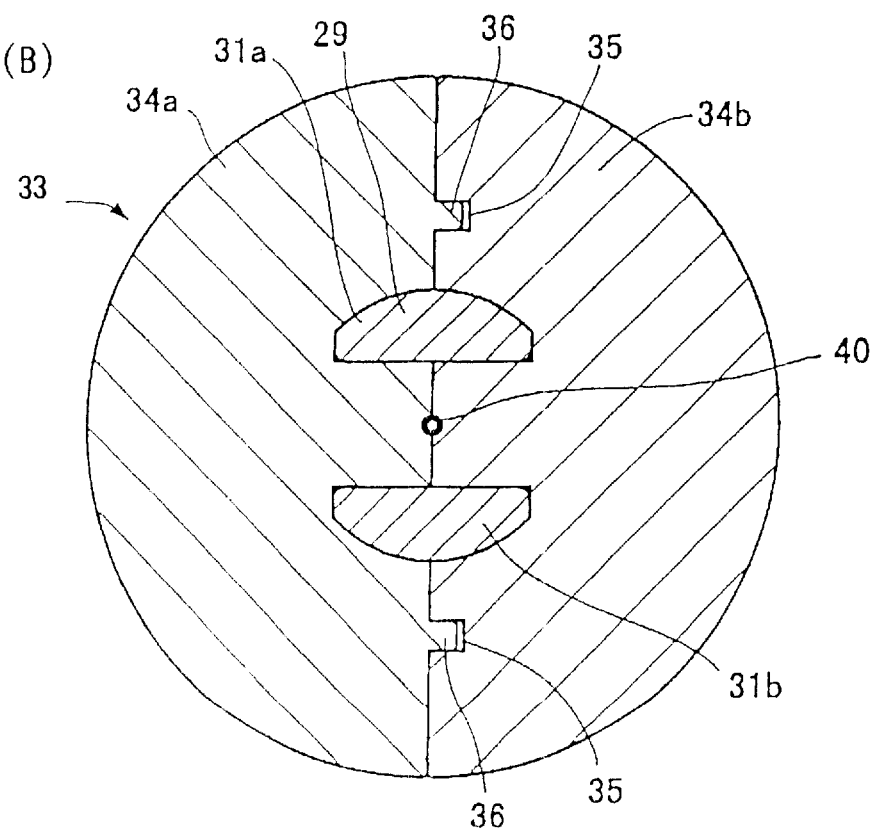
FIG. 10(B) illustrates a sectional view of the slider and the operation part of FIG. 8 taken along the line 10B—10B.

As shown in FIG. 10B), the two members 34a, 34b are joined. The engaging projection 36 of member 34a is engaged into the engaging cavity 35 of member 34b. In this state, the two members 34a, 34b are joined, by means of ultrasonic welding or the like wherein the projection 37 on the two members 34a, 34b melts. The cavity 38 prevents the joint portion from having a clearance when the projection 37 melts.

The slider main body 33 has a portion 39 connecting to the proximal ends of the operation wires 5, 6 at the shaft center. As shown in FIGS. 8, 9, 10(A) and 10(B), the proximal ends of the operation wires 5, 6 are arranged in an operation pipe 40 whose proximal end is engaged into a cylindrical stopper 41. Moreover, the operation wires 5, 6 and the operation pipe 40 and the stopper 41 are integrally joined, for example, by means of caulking, blazing, soft soldering and ultrasonic welding or the like.

An engaging cavity 42 engaging with the stopper 41 is formed at the shaft center of the slider main body 33. While the stopper 41 engages with the engaging cavity 42 of the two members 34a, 34b, the connecting portion 39 is formed at the shaft center of the slider main body 33. The two members 34a, 34b preferably have the same shape.

The axial sliding of the slider 30 along the main body 29 of the operation part 3 moves the two operation wires 5, 6 forward and backward, thereby opening and closing the cup portions 16 of the bioptome cups 13, 14.

Figure 11:
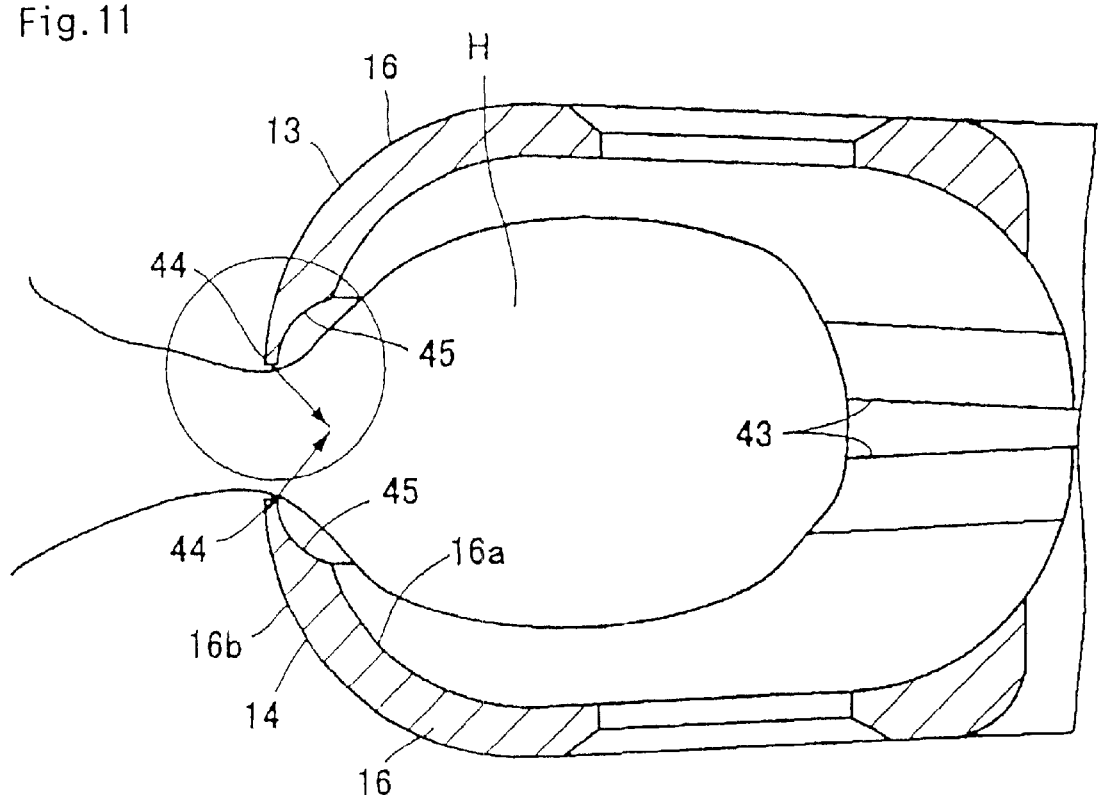
FIG. 11 illustrates a vertical section wherein the bioptome cups are closed and tissue is fastened in a bioptome according to the first embodiment.
Figure 12:
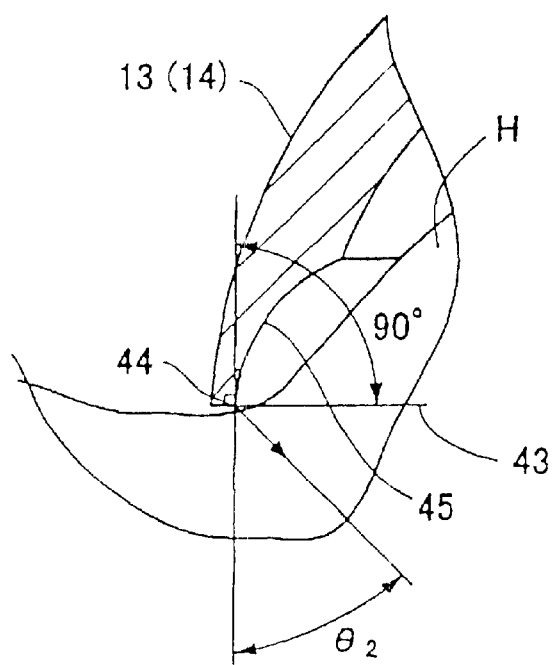
FIG. 12 illustrates a vertical section showing the structure of inner cutting blades in the bioptome cups of a bioptome according to the first embodiment.

As shown in FIG. 11, the bioptome cups 13, 14 have an inner cutting blade 44 on the rim of an opening 43 in the cup portion 16. The inner surface of the cup portion 16 includes a concave section 45 which is approximately arcuate in section near the opening 43, as shown in FIG. 12. The inner cutting blade 44 is formed on the rim of the opening 43 defined by the concave section 45. Therefore, the inner cutting blade 44 of the cup portion 16 deviates from the inner surface 16a towards an outer surface 16b.

As shown in FIG. 12, the inner cutting blade 44 is preferably designed to be at approximately 90° to the plane along the rim of the opening 43 of the cup portion 16. In this case, the angle of the inner cutting blade 44 may be from about 85° to about 180°. The greater the angle is, the better the cup fastens tissue. In this embodiment, the angle is approximately 90° for ease in fabrication (processing). Furthermore, the cutting blade 44 does not have to be formed on the whole rim of the opening 43, as shown in FIG. 2(C).

Figure 7B:
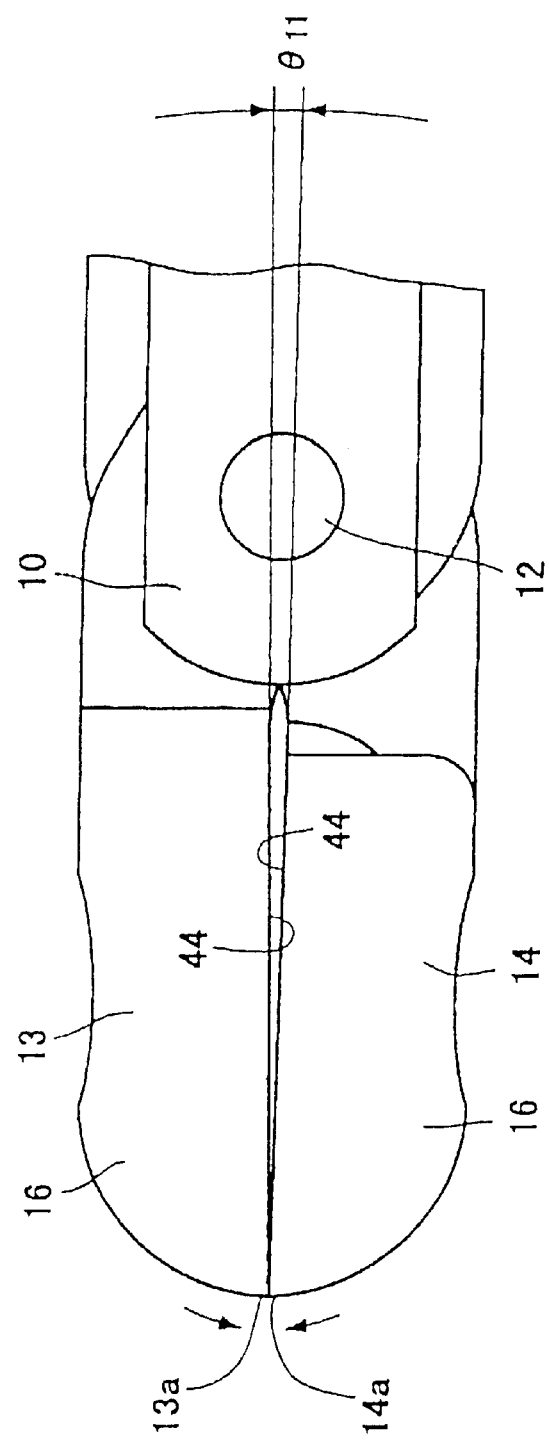
FIG. 7(B) illustrates a side view wherein the distal ends of bioptome cups are engaged in the bioptome according to the first embodiment.

As shown in FIG. 7(A), the face of each cutting blade 44 of bioptome cups 13, 14 is offset an appropriate amount S1 at the right angle to the center line CL1, from the center line CL1 of the insertion part 2 through the center position of the pin 12. This offset makes it possible that the cutting blades 44 hit first at two distal ends 13a, 14a of the bioptome cups 13, 14 when the cups 13, 14 are operated to close, as shown in FIG. 7(B). Therefore, the assembly process can be simplified, although steps are necessary to let the cutting blades 44 hit at the ends of the cups 13, 14 in a conventional bioptome.

As shown in FIG. 7(B), moreover, the inclination angle of the face of cutting blades 44, θ 11, should be more than 0°, and preferably less than 1° when the cutting blades 44 hit at the ends 13a, 14a. The bioptome cups 13, 14 are made of metal such as stainless steel. The surface thereof may be processed with nitrogen to improve the hardness and the strength.

A cap (not shown) is attached to the ends of bioptome cups 13, 14 so that the bioptome cups 13, 14 and the needle member 15 will not damage packing materials when the bioptome 1 is packed. This cap may be made of anything, which can protect packing materials. In order to lower costs, however, a tube of such resin as polyolefin, fluororesin, polyamide, silicon and latex may be cut and used.

The operation of the endoscopic treating instrument according to the first embodiment will now be explained. In a bioptome 1 according to the first embodiment, a slider 30 of the operation part 3 axially slides along the guide rail portions 31a, 31b of the operation main body 29. This movement makes the two operation wires 5, 6 move forward and backward. The cup portions 16 of the bioptome cups 13, 14 are operated to open and close by the movement of the operation wires 5, 6.

As shown in FIG. 11, to use the bioptome 1, tissue H is fastened between the cup portions 16 of two bioptome cups 13, 14 and a part of the tissue H is accommodated there. In this state, by closing the cup portions 16, the inner cutting blades 44 of the cup portions 16 cut the tissue H.

In this embodiment, the angle of the cutting blade 44 arranged on the rim of the cup portion 16 is formed approximately 90° to the plane along the rim of the opening 43. Therefore, the cutting blade 44 can be directed to such a direction that tissue H is securely captured, when the cup portions 16 are closed, as arrow S shows in FIG. 12.

The effect of the endoscopic treating instrument according to the first embodiment will now be explained. In the first embodiment, the angle of the cutting blades 44 arranged on the rim of the cup portion 16 is formed approximately 90° to the plane along the rim of the opening 43. Therefore, the cutting blade 44 can be directed to such a direction that tissue H is securely captured, when the cup portions 16 are closed, as arrow S shows in FIG. 12. The tissue H can be firmly fastened between the cup portions 16 and does not easily come off the cup portions 16 when the inner cutting blades 44 of the cup portions 16 cut the tissue H. As a result, a large part of tissue H can be obtained to easy pathologic diagnosis.

Furthermore, the tissue H does not easily slide and is therefore not crushed on a biopsy for easy pathologic diagnosis. Since the inner cutting blades 44 have a simple shape, additionally, the cutting for forming the cutting blade 44 on the cup portion 16 can be easily done. Accordingly, costs can therefore be lowered.

In the first embodiment, the inner surface 16a of the cup portion 16 includes a concave section 45 which is approximately arcuate in shape in section near the opening 43, as shown in FIG. 12. The rim of the opening 43 in the concave 45 forms the inner cutting blade 44 of the cup portion 16. Therefore, the volume inside the cup portions 16 is increased to increase the size of the obtained tissue on a biopsy.

In the first embodiment, the inner surface 16a of the cup portion 16 includes a concave section 45 which is approximately arcuate in shape in section near the opening 43 whose rim in the concave section 45 forms the inner cutting blade 44 of the cup portion 16, as shown in FIG. 12. However, the first embodiment illustrates a preferable configuration of the inner cutting blade 44. Those skilled in the art will appreciate that other configurations are possible, some of which are illustrated in FIGS. 13(A)–13(D). FIG. 13 (A) shows a first variation of the cutting blade 44 in the inner surface 16a of the cup portion 16. In the first variation, the inner surface 16a of the cup portion 16 has a concave section 46 that is approximately step shaped in section near the opening 43. The rim of the opening 43 in the concave section 46 forms the inner cutting blade 44 of the cup portion 16. Also in this modification, the volume inside the cup portion 16 can be large to increase obtained tissue, since the concave 46 is formed in the inner surface 16a of the cup portion 16. In Table 1, θ is the angle of the cutting blades 44 to the rim face of the cups 13, 14. Table 1 shows obtained tissue amounts and the ease of cutting process in the cups 13, 14 according to the change of θ.

TABLE 1

| θ (°) | Obtained tissue amount | Ease of process |
| --- | --- | --- |
| 70 | Δ | ○ |
| 75 | Δ | ○ |
| 80 | Δ | ○ |
| 85 | ○ | ○ |
| 90 | ○ | ○ |
| 95 | ◎ | Δ |
| 100 | ◎ | x |

The marks in Table 1 indicate the evaluations of "very good" for "◎", "good" for "○", "normal" for "Δ", "bad" for "x".

In view of the results in Table 1, when the angle θ of the cutting blade is 85° and more, the obtained tissue amount increases to be "good". When the angle is 95° and more, the tissue amount increases very much to be "very good", that is, the obtained tissue amount is very large. The ease of process is "good" until the angle θ rises up to 90°. However, when the angle θ becomes over 90°, the ease of process worsens gradually. Over 95° θ makes the ease of process become very bad. According to these results, the angles from about 85° to about 95° realize that the amount of obtained tissue is increased while the ease of process is good.

Figure 13A:
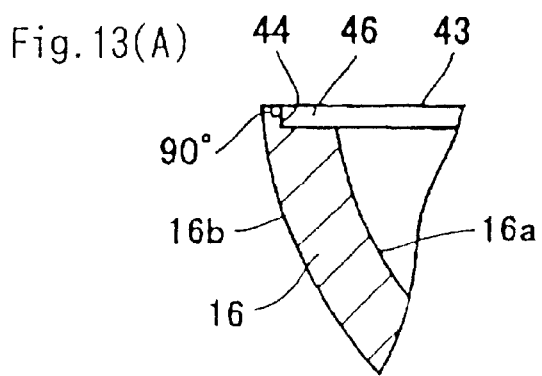
FIG. 13(A) illustrates a vertical section showing a first variation of the bioptome cup according to the first embodiment.
Figure 13B:
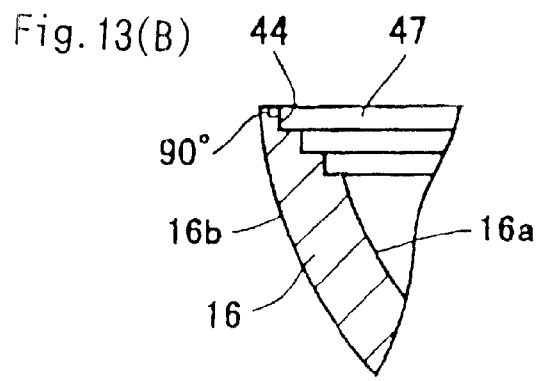
FIG. 13(B) illustrates a vertical section showing a second variation of the bioptome cup according to the first embodiment.

FIG. 13(B) shows the second variation of the cutting blades 44 of the first embodiment. The inner surface 16a has a concave section 47a including a plurality of steps 47b, 47c near the opening 43. In this variation, three steps are provided. The rim of the opening 43 in the concave section 47a forms the inner cutting blade 44 of the cup portion 16. Also in this case, the volume inside the cup portion 16 is increased to obtain an increased amount of tissue, since the concave section 47a is formed in the inner surface 16a of the cup portion 16.

Figure 13C:
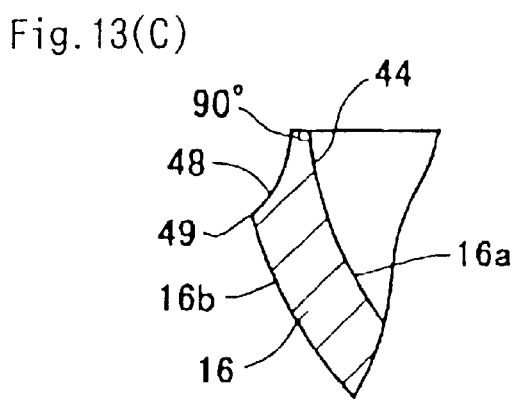
FIG. 13(C) illustrates a vertical section showing a third variation of the bioptome cup according to the first embodiment.

FIG. 13(C) shows the third variation of the cutting blades 44 of the first embodiment. The outer surface 16b of the cup portion 16 has a concave section 48 which is an approximately arc shape in section near the opening 43. The inner cutting blade 44 of the cup portion 16 is formed around the opening 43 in the inner surface 16a intersecting the rim of the opening 43 in the concave section 48. In this case, the sharpness improves since the thickness of the cutting blade 44 is thinner than the thickness between the inner surface 16a and the outer surface 16b.

Figure 13D:
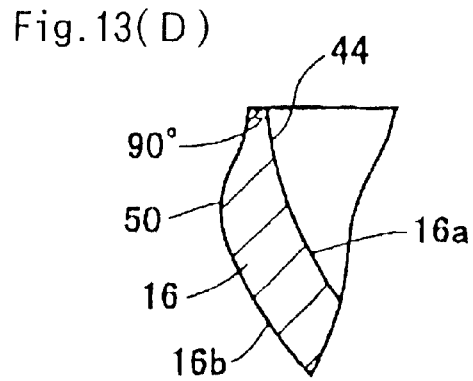
FIG. 13(D) illustrates a vertical section showing a fourth modification of the bioptome cup according to the first embodiment.

FIG. 13(D) shows a fourth variation of the cutting blades 44 of the first embodiment. A smooth arc 50 is formed by cutting a corner 49 between the outer surface 16b and the concave 48 according to the third variation in FIG. 13(C). In this modification, the smooth arc 50 can be contacted to a forceps channel of an endoscope. Since the corner 49 does not get caught in the inner wall face of the endoscope forceps channel, the forceps channel is prevented from being damaged.

FIGS. 14–19 show a second embodiment of the present invention. In the second embodiment, the bioptome cups 13, 14 of the bioptome 1 according to the first embodiment shown in FIGS. 1–12 are changed as follows. Although the bioptome is described as an example in this embodiment, as discussed above, other instruments such as hot biopsy forceps and holding forceps may also be used.

Figure 14:
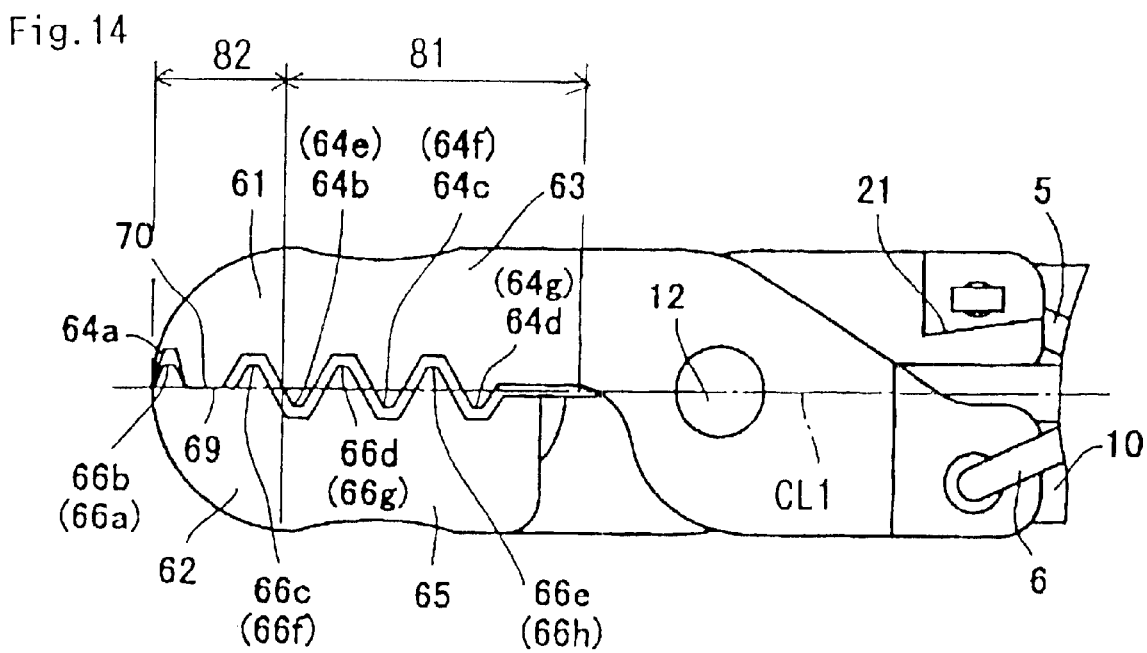
FIG. 14 illustrates a side view showing bioptome cups of a bioptome according to a second embodiment.
Figure 15:
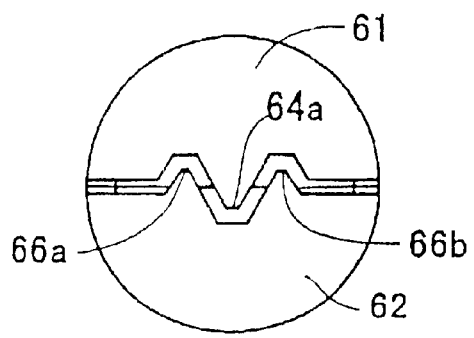
FIG. 15 illustrates a front view of the bioptome cups of the bioptome according to the second embodiment of FIG. 14.
Figure 16:
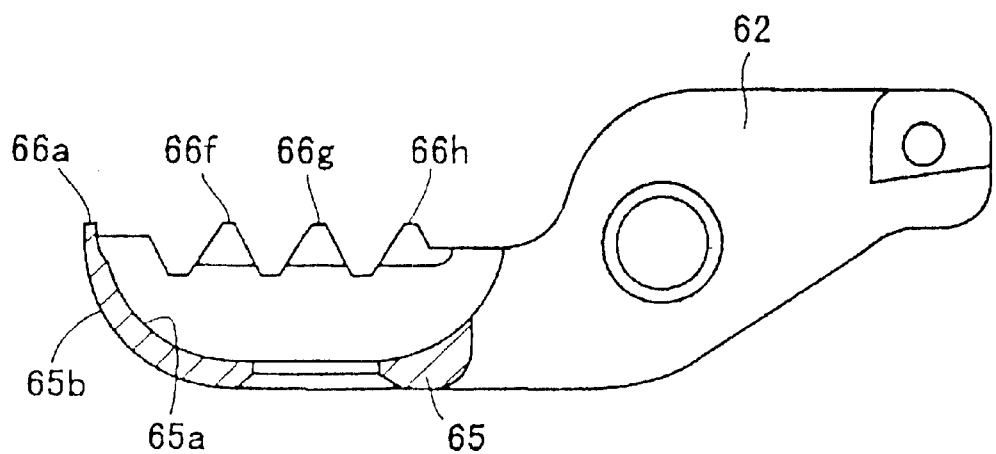
FIG. 16 illustrates a side view partly in section showing the cup portion of the bioptome cup in the bioptome according to the second embodiment of FIG. 14.

Bioptome cups 61, 62 have approximately V-shaped teeth. In FIGS. 14 and 15, V-shaped teeth 64a–64g are downward formed on the rim of the opening of a cup portion 63 in the upper bioptome cup 61. Moreover, in FIGS. 14 and 15, eight V-shaped teeth 66a–66h are upward formed on the rim of the opening of a cup portion 65 in the lower bioptome cup 62. The teeth 66a–66h engage with the teeth 64a–64g of the upper bioptome cup 61.

Figure 17:
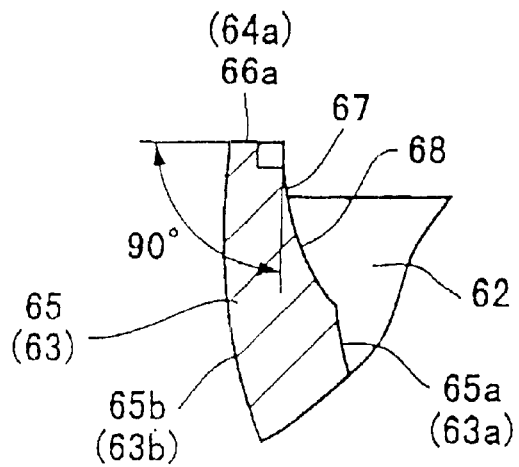
FIG. 17 illustrates a vertical section showing the structure of the inner cutting blade in the bioptome cup according to the second embodiment.

An inner cutting blade 67 is provided to the V-shaped teeth 64a–64g of the upper bioptome cup 61 and the V-shaped teeth 66a–66h of the lower bioptome cup 62. As shown in FIG. 17, the angle of each cutting blade 67 of the V-shaped teeth 64a–64g and 66a–66h is approximately 90°. In addition, as shown in FIG. 17, a concave section 68 which is approximately arcuate in shape is formed near the end in the inner surface of the V-shaped teeth 64a–64g and 66a–66h. The rim on the end of the concave 68 forms the inner cutting blade 67. Thus, the inner cutting blades 67 of the V-shaped teeth 64a–64g, 66a–66h deviate outward from inner surfaces 63a, 65a toward outer surfaces 63b, 65b.

As discussed above with regard to the first embodiment, the angle of each inner cutting blade 67 of the V-shaped teeth 64a–64g and 66a–66h may be from about 85° to about 180°. In this embodiment, the angle is designed about 90° for ease of fabrication.

As shown in FIG. 14, an abutment portion 69 abutting on the lower bioptome cup 62 is formed between the front V-shape tooth 64a and the second V-shaped teeth on both sides in the upper bioptome cup 61. The abutment portion 69 is almost straight. An abutment portion 70 being almost straight is formed in the lower bioptome cup 62 as well. The abutment portion 70 abuts on the abutment portion 69 of the upper bioptome cup 61.

These abutment portions 69, 70 are offset on the same plane as the center line CL1 of the insertion part 2 through the center of the pin 12 of the bioptome cups 61, 62 or at a position exceeding the center line CL1. In the latter case, the abutment portion 69 of the upper bioptome cup 61 is below the center line CL1 and the abutment portion 70 of the lower bioptome cup 62 is above the line.

In this embodiment, as well as the first embodiment, as shown in FIG. 17, the angle of inner cutting blades 67 of the V-shaped teeth 64a–64g, 66a–66h is about 90°. Therefore, the inner cutting blade 67 is directed to such a direction that the tissue H is securely captured when the cups 61, 62 are closed.

Moreover, as shown in FIGS. 14, 15, the seven V-shaped teeth 64a–64g are downward formed in the cup portion 63 of the upper bioptome cup 61, and the eight V-shaped teeth 66a–66h are upward formed in the cup portion 65 of the lower bioptome cup 62. As a result, the cups bite tissue more effectively.

Figure 18:
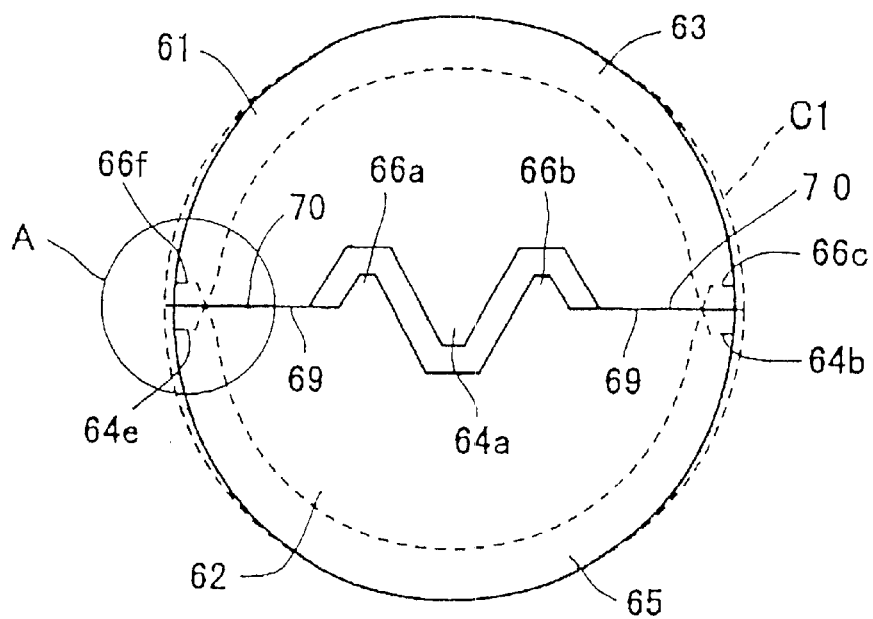
FIG. 18 illustrates a front view of bioptome cups showing a structure in which the cutting blades do not bulge out of a circumscribed circle of the bioptome cups in a bioptome according to the second embodiment.
Figure 19:
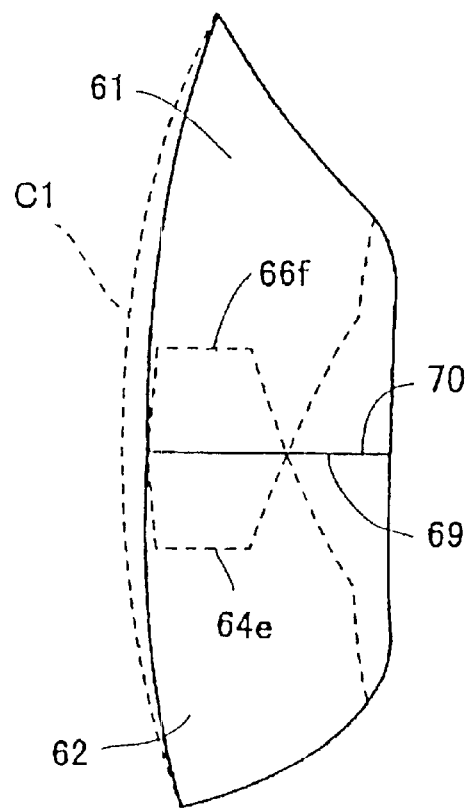
FIG. 19 illustrates an enlarged view of detail A in FIG. 18.

In this embodiment, the abutment portion 69 of the upper bioptome cup 61 and the abutment portion 70 of the lower bioptome cup 62 are offset on the same plane as the center line CL1 of the insertion part 2 through the center of the pin 12 of the bioptome cups 61, 62 or at a position exceeding the center line CL1. In the latter case, the abutment portion 69 of the upper bioptome cup 61 is below the center line CL1 and the abutment portion 70 of the lower bioptome cup 62 is above the center line CL1. As shown in FIG. 18, therefore, the V-shaped teeth 64a–64g and 66a–66h are prevented from outwardly exceeding the circumscribed circle C1 of the cup portions 63, 65, when the abutment portion 69 of the upper bioptome cup 61 abuts on the abutment portion 70 of the lower bioptome cup 62. FIG. 19 is an enlarged view of detail A in the circle of FIG. 18. FIG. 18 shows that V-shaped teeth 64a–64g, 66a–66h do not outwardly exceed the circumscribed circle C1 of the cup portions 63, 65.

Figure 20:
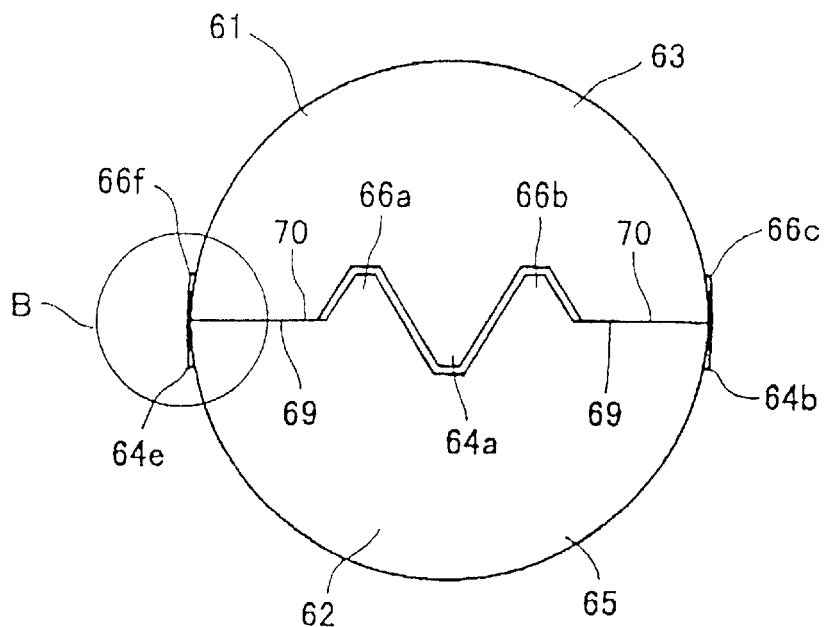
FIG. 20 illustrates a front view of bioptome cups in which the cutting blades bulge out of the circumscribed circle of bioptome cups in a bioptome.
Figure 21:
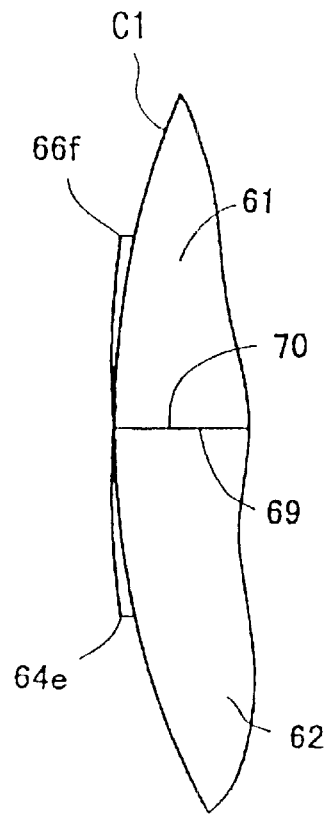
FIG. 21 illustrates an enlarged view of detail B in FIG. 20.

The abutment portion 69 of the upper bioptome cup 61 and the abutment portion 70 of the lower bioptome cup 62 are offset as shown in FIG. 7(A). In this case, as shown in FIG. 20, the V-shaped teeth 64a–64g and 66a–66h outwardly exceed the circumscribed circle C1 of the cup portions 63, 65, when the abutment portion 69 of the upper bioptome cup 61 abuts on the abutment portion 70 of the lower bioptome cup 62. FIG. 21 is an enlarged view of detail B in the circle of FIG. 20. FIG. 21 shows that V-shaped teeth 64a–64g, 66a–66h outwardly exceed the circumscribed circle C1 of the cup portions 63, 65.

In this embodiment, however, the V-shaped teeth 64a–64g of the upper bioptome cup 61 and the V-shaped teeth 66a–66h of the lower bioptome cup 62 are prevented from outwardly exceeding the circumscribed circle C1 of the cup portions 63, 65. Therefore, the portion exceeding the circumscribed circle C1 of the cup portions 63, 65 do not get caught in the inner wall face of endoscope forceps channel and the forceps channel is prevented from being damaged.

Figure 22:
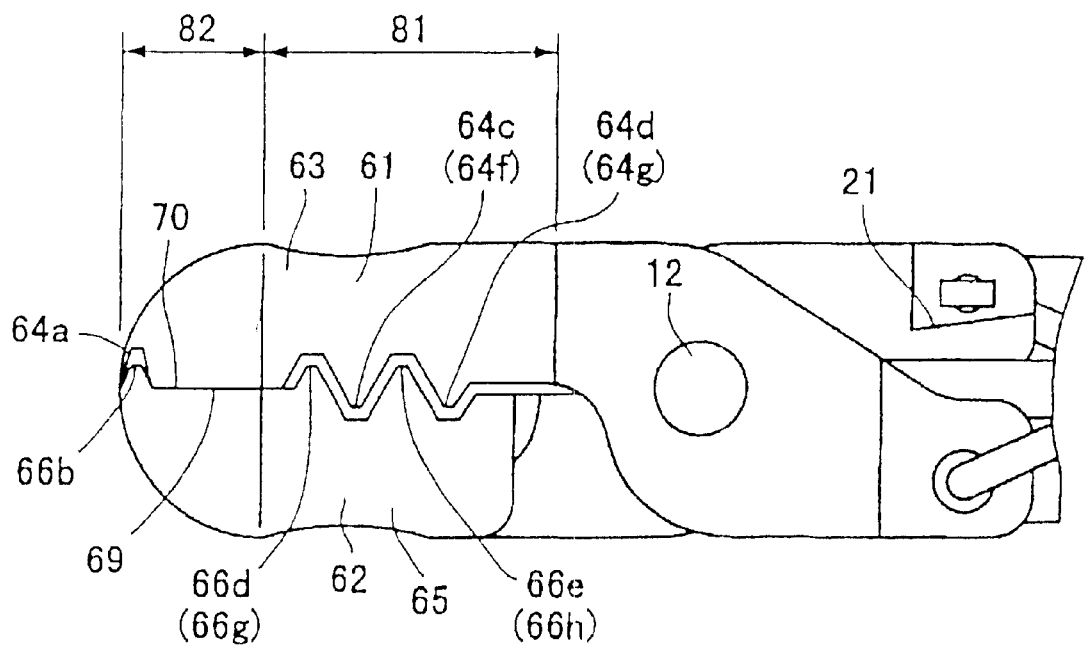
FIG. 22 illustrates a side view showing bioptome cups in a bioptome according to a third embodiment.
Figure 23:
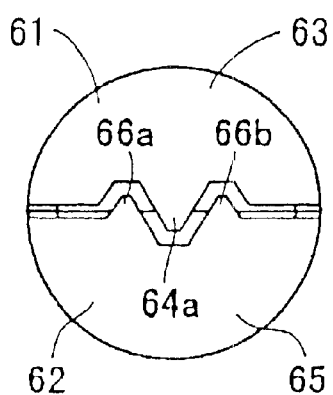
FIG. 23 illustrates a front view of the bioptome cups of the bioptome according to the third embodiment of FIG. 22.
Figure 24:
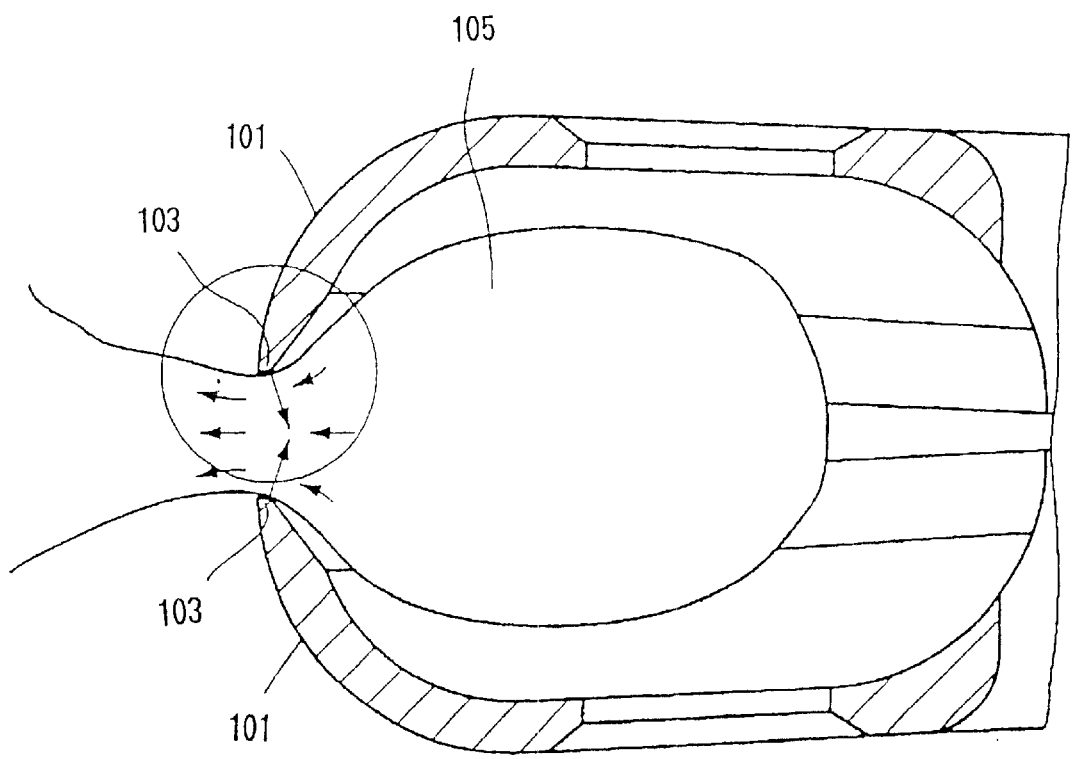
FIG. 24 illustrates a vertical section showing the state in which bioptome cups of a conventional bioptome are closed and tissue is fastened.
Figure 25:
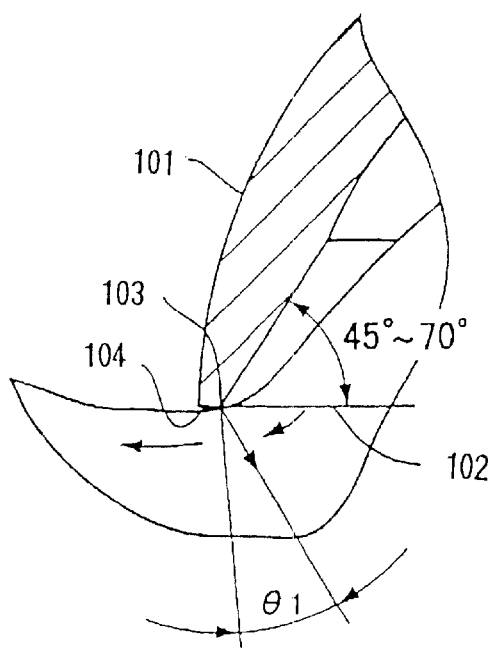
FIG. 25 illustrates a vertical section showing the structure of inner cutting blades in the bioptome cups of the bioptome in FIG. 25.

FIGS. 22 and 23 illustrate a third embodiment of the present invention. In this embodiment, the structure of bioptome cups 61, 62 of the endoscopic bioptome 1 according to the second embodiment in FIGS. 14–19 is changed as follows.

As shown in FIG. 22, the cup portions 63, 65 of the third embodiment has a spherical portion 82 formed on the distal end of a cylindrical portion 81. The spherical portion 82 does not include the V-shaped teeth 64b, 64e of the bioptome cup 61 and 66c, 66f of the bioptome cup 62 so that the abutment portions 69, 70 are extended.

In this embodiment, for example, when the bioptome cups 61, 62 in FIG. 14 deviate in the axial direction of the pin 12, the V-shaped teeth 64b, 64e and 66c, 66f formed on the spherical portion 82 do not get caught in the inner wall face of endoscope forceps channel, and the forceps channel is prevented from being damaged. The safety of the endoscopic bioptome 1 can be improved further in this embodiment, therefore.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscopic treating instrument comprising:
 a flexible insertion part having a hollow section;
 an operation wire provided in the hollow section of said insertion part and movable forward and backward in an axial direction of said insertion part;
 an operation part which is connected to a proximal end of said insertion part for moving said operation wire forward and backward; and
 a bioptome member mounted to a distal end of said insertion part, said bioptome member having a cup portion, said cup portion having an inner cutting blade formed on a rim thereof, an angle $\theta$ of said cutting blade being formed from about 85° to about 110° to a plane along the rim of said cup portion.

2. The endoscopic treating instrument according to claim 1, wherein said inner cutting blade deviates outward from an inner surface.

3. The endoscopic treating instrument according to claim 1, wherein an outer surface of said cup portion is formed without an edge such that the thickness of said cutting blade is thinner than that of said cup portion between the inner surface and the outer surface.

4. The endoscopic treating instrument according to claim 1, wherein said angle $\theta$ is about 90°.

5. The endoscopic treating instrument according to claim 1, wherein said bioptome member is made of metal.

6. The endoscopic treating instrument according to claim 1, wherein said bioptome member is made of resin.

7. The endoscopic treating instrument according to claim 1, wherein said cup portion has an approximately hemispherical distal end and an approximately cylindrical proximal end which are divided lengthwise, said cup portion further having at least one V-shaped tooth on one of the distal end or sides of said rim, and said cutting blade is formed on at least one of said tooth.

8. The endoscopic treating instrument according to claim 7, wherein the tooth on the side of said cup portion among said V-shaped teeth is formed proximate to said hemispherical distal end of said cup portion.

9. The endoscopic treating instrument according to claim 1 comprising a pair of said bioptome members.

10. The endoscopic treating instrument according to claim 9, wherein said pair of bioptome members are the same shape.

11. The endoscopic treating instrument according to claim 1, wherein said bioptome member is formed by cutting.

12. The endoscopic treating instrument according to claim 1, wherein said bioptome member is formed by metal injection molding or casting.

13. The endoscopic treating instrument according to claim 1, wherein said bioptome member is formed by cold forging.

14. The endoscopic treating instrument according to claim 1, wherein said bioptome member is fabricated from a group consisting of stainless steel, aluminum, nickel, brass, titanium, iron, phosphor bronze, tungsten, gold, silver, copper or alloys thereof.

15. The endoscopic treating instrument according to claim 13, wherein said bioptome member is formed by pressing plate metal.

16. The endoscopic treating instrument according to claim 1, wherein the surface of said bioptome member is processed with nitrogen.

17. The endoscopic treating instrument according to claim 1, wherein said bioptome member further comprises a gold plating.

18. The endoscopic treating instrument according to claim 17, wherein said bioptome member further comprises a P—Ni alloy, matte Ni, and gold laminate plating.

19. An endoscopic treating instrument comprising:
 a body;
 at least one member pivotally connected to a distal end of said body, each of said at least one member further having a cup portion defined by a rim, said rim having an inner cutting blade formed at least partly thereon, an angle $\theta$ of said cutting blade being formed from about 85° to about 110° to a plane along said rim of said cup portion; and
 a handle part having means for actuating said at least one member between open and closed positions.

20. The endoscopic treating instrument according to claim 19, wherein said at least one member comprises two members, each of which is actuated by said handle part between said open and closed positions.

* * * * *